(12) United States Patent
Anderson et al.

(10) Patent No.: US 7,220,778 B2
(45) Date of Patent: May 22, 2007

(54) METHODS AND DEVICES FOR EPITHELIAL PROTECTION DURING PHOTODYNAMIC THERAPY

(75) Inventors: Richard Rox Anderson, Lexington, MA (US); Bernhard Ortel, Boston, MA (US); Eliot F. Battle, Washington, DC (US); Edwin K. Joe, New York, NY (US)

(73) Assignee: The General Hospital Corporation, Boston, MA (US)

( * ) Notice: Subject to any disclaimer, the term of this patent is extended or adjusted under 35 U.S.C. 154(b) by 441 days.

(21) Appl. No.: 10/709,121

(22) Filed: Apr. 14, 2004

(65) Prior Publication Data

US 2004/0259854 A1 Dec. 23, 2004

Related U.S. Application Data

(60) Provisional application No. 60/462,937, filed on Apr. 15, 2003.

(51) Int. Cl.
*A61K 31/195* (2006.01)
*A61K 9/127* (2006.01)
*A01N 43/42* (2006.01)

(52) U.S. Cl. ............ 514/561; 514/563; 514/538; 514/183; 504/130; 504/147; 424/450

(58) Field of Classification Search .......... 514/561, 514/563, 538, 183; 504/130, 147; 424/450
See application file for complete search history.

(56) References Cited

U.S. PATENT DOCUMENTS

| | | | |
|---|---|---|---|
| 5,451,576 A | 9/1995 | Sessler et al. | |
| 5,474,528 A * | 12/1995 | Meserol | ............ 604/20 |
| 5,643,334 A | 7/1997 | Eckhouse et al. | |
| 5,784,162 A | 7/1998 | Cabib et al. | |
| 5,976,535 A * | 11/1999 | Fritzberg et al. | ...... 424/182.1 |
| 6,096,030 A * | 8/2000 | Ortiz | ............ 606/14 |
| 6,099,521 A | 8/2000 | Shadduck | |
| 6,162,242 A | 12/2000 | Peyman | |
| 6,180,402 B1 | 1/2001 | Granville et al. | |
| 6,358,242 B1 | 3/2002 | Cecchetti | |
| 6,365,145 B1 | 4/2002 | Ben-Hur et al. | |
| 6,380,254 B2 * | 4/2002 | Pearlstein et al. | ........ 514/561 |
| 6,443,976 B1 | 9/2002 | Flower et al. | |
| 2001/0027206 A1* | 10/2001 | Pearlstein et al. | ........ 514/400 |
| 2002/0127230 A1 | 9/2002 | Chen | |
| 2004/0259854 A1* | 12/2004 | Anderson et al. | ........ 514/185 |
| 2006/0004347 A1* | 1/2006 | Altshuler et al. | ......... 606/4 |

OTHER PUBLICATIONS

Paul et al., Alkyl-substituted magnesium phthalocyanine . . . (abstract only), Database CAPLUS AN:10752, Journal of Porphyrins and phthalocyanines, 2002, vol. 6(5), pp. 340-346.*
Wyld et al., The influence of hypoxia and pH on aminoaevulinic acid . . . , (abstract only) Database CAPLUS AN 1998:384288, British Journal of Cancer, 1998, vol. 77(10), pp. 1621-1627.*
Chen et al., Oxygen effect of photodynamic therapy, (abstract only) Database CAPLUS AN 1997:415867, Proceedings of SPIE-The International Socierty for optical Engineering , 1997, vol. 2972, pp. 80-87.*
Gonzalez et al., Treatment of Dunning R3327-AT rat prostate tumors . . . , (abstract only) Database CAPLUS AN 1986:438348, Cancer Research, 1986, vol. 46(6), pp. 2858-2862.*

* cited by examiner

*Primary Examiner*—Vickie Kim
(74) *Attorney, Agent, or Firm*—Nutter, McClennen & Fish, LLP

(57) ABSTRACT

Methods for preventing damage to epithelial tissue during PDT induced using a photosensitizing agent or pre-photosensitizing agent are provided. The methods of the present invention utilize spatial confinement to control photoactivation of the photoactive species to protect the epithelial tissue. In one embodiment, epithelial tissue surrounding a targeted treatment site can be protecting by decreasing the oxygen-content in the tissue, thereby preventing the conversion of the photosensitizer into the phototoxic species in the epithelial tissue.

13 Claims, 2 Drawing Sheets

METHODS AND DEVICES FOR EPITHELIAL PROTECTION DURING PHOTODYNAMIC THERAPY

CROSS REFERENCE TO RELATED APPLICATIONS

This application claims priority from U.S. Provisional Patent Application Ser. No. 60/462,937, filed on Apr. 15, 2003, entitled "Methods for Epidermal Protection During Photodynamic Therapy," which is expressly incorporated by reference herein.

FIELD OF THE INVENTION

The present invention relates to methods and devices for protecting epithelial tissue during photodynamic therapy, and in particular to methods and devices for reducing phototoxicity during photodynamic therapy.

BACKGROUND OF THE INVENTION

Photodynamic therapy (PDT), which can be used for many purposes including hair removal and acne treatment, involves the combination of a light-absorbing photosensitizing agent with light of the appropriate wavelength. A pre-photosensitizer, such as aminolevulinic acid (ALA, ALA-ester), which converts into a photosensitizing agent when it metabolizes, can also be used. The photosensitizing agent or pre-photosensitizing agent is topically or systemically applied to a target tissue where it accumulates. Upon irradiation with a visible light of an activating wavelength, the photosensitizing agent causes the release of reactive oxygen species in cells containing the photosensitizing agent, thereby promoting cell death.

While PDT induced using a photosensitizing agent or pre-photosensitizing agent has been somewhat successful, it can be difficult to control the treatment area. In particular, the photosensitizing agent or pre-photosensitizing agent can accumulate in healthy tissues as well as the target tissue. In hair removal, for example, the photosensitizing agent or pre-photosensitizing agent is applied to the skin topically and is absorbed by both the epidermal and dermal layers of the skin. As a result, application of light can cause phototoxicity to the epidermis, which can lead to long-lasting hyperpigmentation or epidermal necrosis.

Accordingly, there is a need for improved methods and devices for photodynamic therapy that reduce or eliminate damage to the epithelial tissue while allowing treatment of underlying targeted tissue.

BRIEF SUMMARY OF THE INVENTION

The present invention generally provides methods and devices for controlling the application of PDT induced using a photosensitizing agent or pre-photosensitizing agent, and in particular for preventing damage to superficial tissue layers, such as the epidermis, during PDT. In one embodiment, the method includes the step of administering an agent to tissue surrounding a targeted treatment site such that a photosensitizing agent accumulates in the tissue. The agent can be a photosensitizing agent, or it can be a pre-photosensitizing agent which metabolizes into a photosensitizing agent as it accumulates in tissue. The method further includes the steps of irradiating the targeted treatment site to activate the in vivo photosensitizing agent to cause phototoxicity, while inhibiting phototoxicity in non-targeted tissue such that the non-targeted tissue is substantially unaffected. The present invention also provides a device that is effective to decrease local circulation and delivery of oxygenated blood and/or to flush the tissue surface with nitrogen.

While various techniques can be used to inhibit activation of the photosensitizing agent, e.g., to inhibit phototoxicity, in the non-targeted tissue, in an exemplary embodiment phototoxicity is inhibited by reducing the oxygen-content in the non-targeted tissue surrounding the targeted treatment site during the step of irradiating the treatment site. The oxygen-content can be reduced, for example, by applying an external vacuum to the non-targeted tissue, by flushing the non-targeted tissue with nitrogen gas, and/or by decreasing local circulation and delivery of oxygenated blood to the non-targeted tissue.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
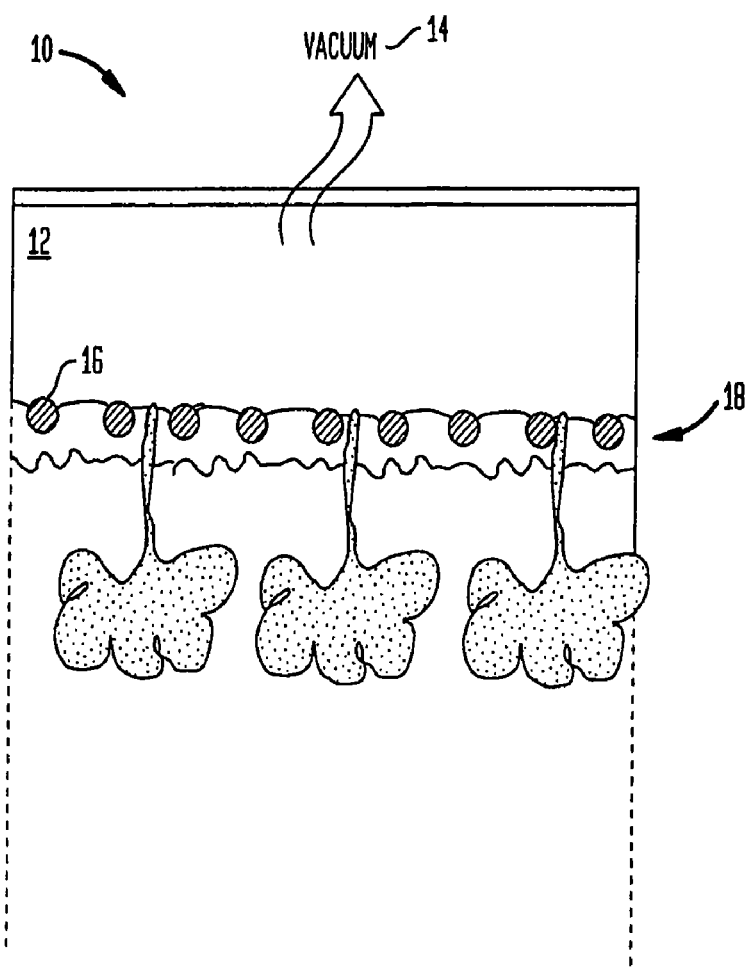
FIG. 1A is a diagram illustrating one embodiment of a device for depriving epidermal tissue of oxygen in accordance with the present invention.

During PDT, a photosensitizing agent or a pre-photosensitizing agent, such as ALA, is administered to the skin surface, e.g., the epidermal tissue, above a targeted treatment site. This allows the photosensitizing agent or pre-photosensitizing agent to be absorbed through the tissue and into tissue at the targeted treatment site, where the agent accumulates in tissue at the targeted treatment site. Where a pre-photosensitizing agent is used, such as ALA, the agent metabolizes into a photosensitizing agent, e.g., a photoactive species, such as the protoporphyrin IX (PpIX), as it accumulates in the tissue. Upon the application of light having an appropriate wavelength, the photosensitizing agent absorbs the light and becomes phototoxic, releasing oxygen to destroy the cells. While ALA-induced PDT has proven effective, the photosensitizing agent or metabolized pre-photosensitizing agent can accumulate in both epithelial tissue and underlying targeted tissue, thereby potentially causing damage to non-targeted, healthy epithelial tissue. The present invention therefore provides methods and devices for preventing or reducing the likelihood of damage to epithelial tissue, such as the epidermis, during PDT, and in particular the present invention provides method and devices for protecting epithelial tissue during PDT in which phototoxicity of the photosensitizing agent is inhibited in non-targeted epithelial tissue during the application of light to a targeted treatment site.

The methods and devices of the present invention can be used with a variety of photosensitizing agents and pre-photosensitizing agents, but in an exemplary embodiment, the methods and devices of the present invention are used with ALA-induced PDT, which is described in more detail in U.S. Patent Publication No. 2002/0099094A1 entitled "Topical Aminolevulinic Acid-Photodynamic Therapy For The Treatment Of Acne Vulgaris." As disclosed therein, ALA can be used in a variety of forms, including in a pharmacologically equivalent form, such as an amide or ester, or as a salt, such as hydrochloride salt, and it can be topically applied to the skin surface surrounding a targeted treatment site, which underlies the epidermal tissue at the skin surface, or it can be administered using other techniques known in the art. A light source, preferably red visible light having a wavelength in the range of about 320 nm to 700 nm, and more preferably about 25 nm to 200 nm, is applied to the targeted treatment site at a dosage of energy in the range of about 1 $J/cm^2$ to 200 $J/cm^2$, and more preferably about 25 $J/cm^2$ to 200 $J/cm^2$. Other suitable photosensitizing agents or pre-photosensitizing agents include, for example, porphyrins, chlorines, porphycenes, purpurins, phthalocyanines, naphthalocyanines, bacteriochlorins, benzophenothiazines, either as free agents or in combination with specific delivery agents such as in liposomes or as photosensitizer conjugates with targeting molecules, such as peptides, receptor ligands or antibodies.

Conversion of the in vivo photosensitizing agent can be inhibited using a variety of techniques, but in an exemplary embodiment the oxygen-content in epithelial tissue, such as epidermal tissue, surrounding a targeted treatment site is reduced. PDT induced using a photosensitizing agent or a pre-photosensitizing agent, such as ALA, requires oxygen for the formation of the reactive oxygen species that destroy the cells when the tissue is irradiated. Thus, the epidermis can be protected during irradiation by reducing the amount of oxygen available to the skin cells in the epidermis. This can be achieved by, for example, spatially depleting the oxygen at the skin surface by flushing the area with nitrogen gas, and/or by decreasing local circulation and delivery of oxygenated blood.

Figure 1B:
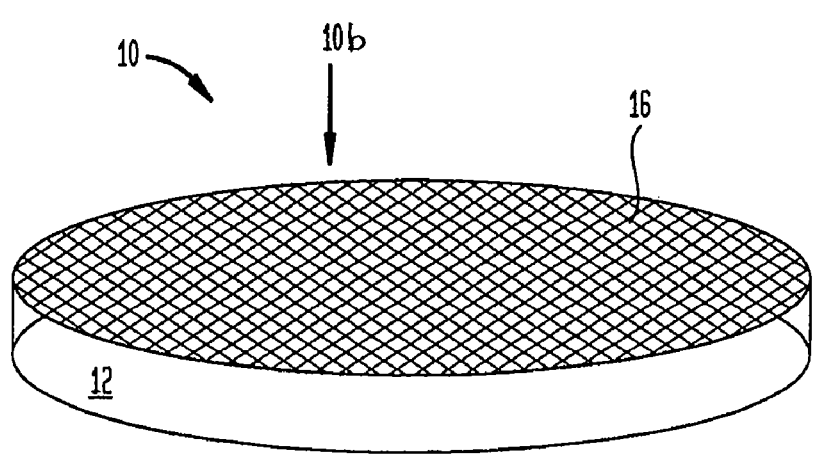
FIG. 1B is a bottom view of the device shown in FIG. 1A.

FIGS. 1A and 1B illustrate one embodiment of a device 10 that can be used to deprive epidermal tissue of oxygen during PDT, thereby protecting the epidermal tissue while allowing PDT of the underlying dermal tissue. In general, the device 10 is adapted to be placed on a tissue surface to seal a portion of the tissue from the external environment. A chamber 12 within the device 10 can be coupled to a vacuum 14 to decrease local circulation and delivery of oxygenated blood, and/or the chamber 12 can be flushed with nitrogen to deprive the tissue surface of oxygen, thereby preventing phototoxicity to the epidermal tissue surface. The device 10 is preferably used simultaneously with the application of light, and thus at least a portion of the device 10 is preferably formed from a material that is transparent to radiating light to allow the tissue underlying the device 10 to be treated while the tissue surface is deprived of oxygen.

While the device 10 can have any shape, size, and configuration depending on the intended use, FIGS. 1A and 1B illustrate a device 10 in the form of a substantially circular housing defining a chamber 12 formed therein. A bottom portion 10b (FIG. 1B) of the housing 10 is adapted to be positioned on a skin surface, e.g., the epidermal tissue surface 18 as shown in FIG. 1A, such that the skin surface 18 is in communication with the chamber 12 and is sealed from the surrounding environment. While the bottom portion 10b can be open, a porous material, such as a wire mesh 16 as shown, preferably extends there across. When at least a partial vacuum is created within the chamber 12, the wire mesh 16 allows the skin to deform there around (shown in FIG. 1A) thereby reducing blood flow to the tissue. The housing 10 can also include a seal (not shown), such as an o-ring, formed on or disposed around a perimeter of the bottom portion 10b to facilitate a secure seal between the housing 10 and the tissue surface.

In use, the housing 10 is positioned on the tissue surface above a targeted treatment site either after or simultaneously with the topical application of a photosensitizing agent. A vacuum or partial vacuum can then be applied to the chamber 12 and/or the chamber 12 can be flushed with nitrogen. The vacuum may be applied by a pump or manually, for example, using a syringe. As a result, the device is further sealed to the tissue by suction and blood flow near the tissue surface is reduced and the tissue is deprived of oxygen. Light exposure for photodynamic therapy is then administered. The photosensitizing agent located in the epidermal tissue is thereby prevented from becoming phototoxic when the tissue is irradiated with light.

The techniques of the present invention can be used in a variety of applications, and they can also be applied in combination with methods for preventing metabolism of a photosensitizing agent in epidermal tissue surrounding the targeted treatment site, as described in a U.S. patent application filed concurrently herewith and titled "Methods for Epidermal Protection During Photodynamic Therapy."

In an exemplary embodiment, the method is used during hair removal to establish an oxygen gradient with relative hypoxia in the interfollicular epidermis to decrease the phototoxic effects of PDT in this skin layer relative to the deeper-seated hair follicles, where phototoxicity is desired. This would allow for the enhanced efficiency of hair removal while minimizing side effects secondary to epidermal damage. Similarly, for acne treatment, epidermal damage would be minimized by allowing targeting of PDT to the deeper sebaceous glands. In another example, establishing a relatively hypoxic environment in the normal tissue surrounding cancerous skin cells would enhance the selectivity of PDT-mediated destruction of neoplastic cells.

The followings examples serve to further illustrate the present invention.

EXAMPLE 1

Figure 2A:
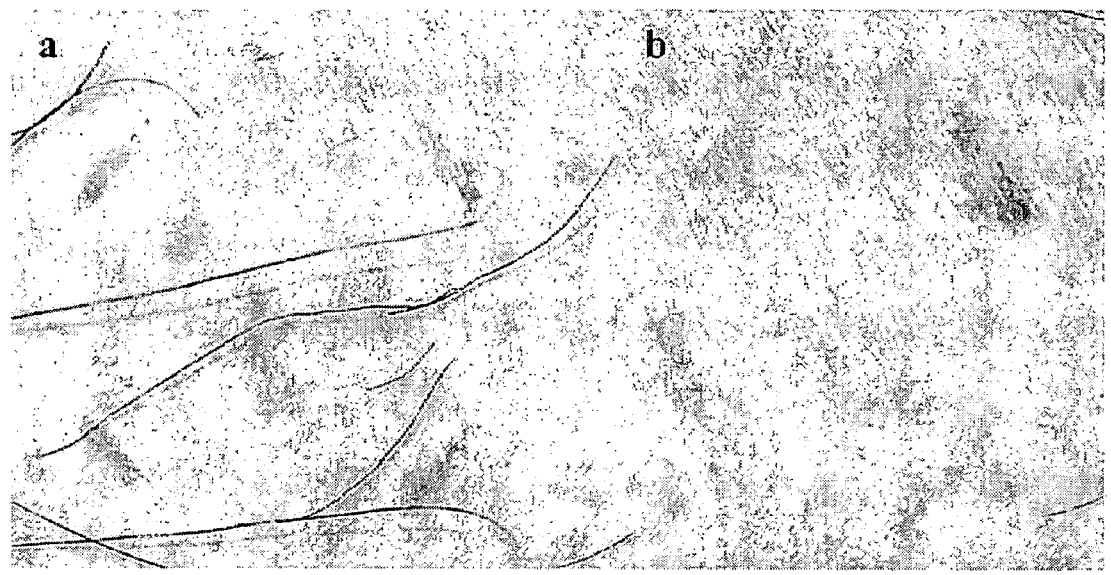
FIG. 2A is a photograph of human skin showing the effect of reduced oxygen on the formation of PpIX in human skin treated with a 2% solution of ALA.
Figure 2B:
FIG. 2B is another photograph of human skin showing the effect of reduced oxygen on the formation of PpIX in human skin treated with a 2% solution of ALA.

ALA was iontophoretically transferred into human skin, followed by incubation for 3 hours. Irradiation was then performed with a 635-nm diode laser on (a) a control, (b) a tourniquet applied to the extremity for 1 minute prior to and during irradiation, (c) a control, and (d) an external vacuum applied to skin. As shown in FIG. 2A, the decreased oxygen in the skin (b) caused by the tourniquet was effective to remove hair, as compared to the control (a), and as shown in FIG. 2B, the decreased oxygen in the skin (d) caused by the external vacuum was effective to remove hair, as compared to the control (c).

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for inhibiting phototoxicity of a photosensitizing agent in non-targeted tissue during photodynamic therapy using the photosensitizing agent or a pre-photosensitizing agent, the method comprising the steps of: administering an agent to a targeted treatment site, the agent being effective to accumulate in tissue at the targeted treatment site as a photosensitizing agent; and irradiating the targeted treatment site to activate the photosensitizing agent to cause phototoxicity in tissue at the targeted treatment site while inhibiting phototoxicity of the photosensitizing agent in non-targeted tissue surrounding the targeted treatment site, wherein the step comprises reducing the oxygen-content in the non-targeted tissue during the step of irradiating the treatment site.

2. The method of claim 1, wherein the step of reducing the oxygen-content in the non-targeted tissue comprises applying an external vacuum to the non-targeted tissue.

3. The method of claim 1, wherein the step of reducing the oxygen-content in the non-targeted tissue comprises the step of flushing the non-targeted tissue with nitrogen gas.

4. The method of claim 3, wherein the non-targeted tissue is flushed with nitrogen gas by positioning a housing having a chamber formed therein on the non-targeted tissue such that the non-targeted tissue is in communication with the chamber, and filling the chamber with nitrogen gas.

5. The method of claim 1, wherein the step of reducing the oxygen-content in the non-targeted tissue comprises the step of decreasing local circulation and delivery of oxygenated blood to the non-targeted tissue.

6. The method of claim 5, wherein local circulation and delivery of oxygenated blood is decreased by positioning a housing having a chamber formed therein on the non-targeted tissue such that the tissue is in communication with the chamber, and creating a vacuum within the chamber.

7. The method of claim 6, wherein the housing includes a porous, tissue-contacting surface such that the tissue deforms around the tissue-contacting surface when a vacuum is created within the chamber.

8. The method of claim 1, wherein the non-targeted tissue comprises epithelial tissue.

9. The method of claim 1, wherein the non-targeted tissue comprises epidermal tissue.

10. The method of claim 1, wherein the agent comprises a photosensitizing agent.

11. The method of claim 1, wherein the agent comprises a pre-photosensitizing agent.

12. The method of claim 11, where the pre-photosensitizing agent is selected from the group consisting of aminolevulinic acid and esters of aminolevulinic acid.

13. The method of claim 1, wherein the agent is selected from the group consisting of porphyrins, chlorines, porphycenes, purpurins, phthalocyanines, naphthalocyanines, bacteriochlorins, benzophenothiazines, and combinations thereof.

* * * * *